US00PP35260P2

(12) United States Plant Patent
Krebs

(10) Patent No.: US PP35,260 P2
(45) Date of Patent: Jul. 11, 2023

(54) MINT PLANT NAMED 'MP18'

(50) Latin Name: ***Mentha suaveolens* x *piperita***
Varietal Denomination: MP18

(71) Applicant: Nathan L. Krebs, Yakima, WA (US)

(72) Inventor: Nathan L. Krebs, Yakima, WA (US)

( * ) Notice: Subject to any disclaimer, the term of this patent is extended or adjusted under 35 U.S.C. 154(b) by 0 days.

(21) Appl. No.: 17/803,604

(22) Filed: Sep. 7, 2022

(51) Int. Cl.
*A01H 5/12* (2018.01)
*A01H 6/50* (2018.01)

(52) U.S. Cl.
USPC ..... Plt./259

(58) Field of Classification Search
USPC ..... Plt./258, 259
See application file for complete search history.

*Primary Examiner* — Susan McCormick Ewoldt
(74) *Attorney, Agent, or Firm* — Svendsen Legal, LLC

(57) ABSTRACT

A new mint plant named 'MP18' is disclosed. 'MP18' is used for its exceptional and unique oil and aromatic qualities, and is suitable for botanical beverage and tea flavoring.

10 Drawing Sheets

Genus and species: *Mentha suaveolens* x *piperita*.
Variety denomination: 'MP18'.

CROSS-REFERENCE TO RELATED APPLICATIONS

None

STATEMENT REGARDING FEDERALLY SPONSORED RESEARCH OR DEVELOPMENT

None

BACKGROUND OF THE INVENTION

'MP18' is a product of a controlled breeding carried out by the inventor in the Yakima Valley of Washington State. 'MP18' was one of several seedlings resulting from a controlled cross made in 2017 with female parent 'MP17'. 'MP17' is a hybrid cross employing a controlled pollination, by crossing *Mentha suaveolens*, common name apple mint which is a commercially available unpatented variety, with female parent *Mentha* x *piperita f. citrata*, common name chocolate mint, which is also commercially available and unpatented. Seedling plants from this cross were planted in 2017 in a greenhouse and field nursery located in the East Selah, near Yakima, Wash. A single plant of 'MP17' was selected as a female parent in 2018 and crossed with pollinator *Mentha suaveolens* var. 'Variegata', an unpatented variety, (common name, pineapple mint) in a controlled cross, which resulted in a refined, new hybrid mint plant, designated 'MP18'. In 2019 'MP18' was asexually reproduced via herbaceous cuttings, and expanded in the evaluation nursery located in East Selah, near Yakima, Wash. Throughout several generations of asexual propagation, 'MP18' has been observed to retain its distinctive characteristics as detailed herein and remain true to type. In April of 2022 'MP18' was further expanded to a one (1) acre test block on a pilot farm also located in East Selah, near Yakima, Wash. for crop expansion, and initial commercial and industrial sales of the 'MP18' rhizome, with approximately 1,000 (one thousand) plants asexually reproduced via herbaceous cuttings.

BRIEF DESCRIPTION OF THE PHOTOGRAPHS

Figure 1:
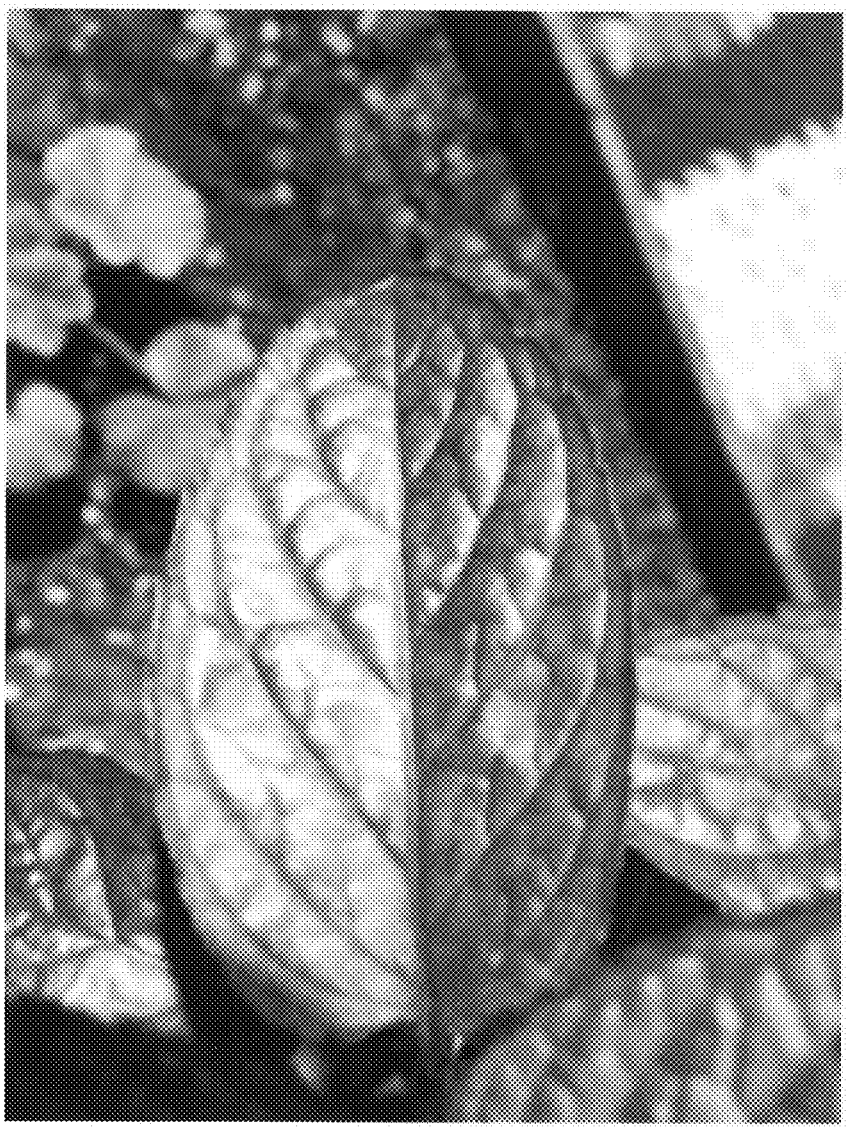
FIG. 1 illustrates a mature leaf of a 'MP18' mint plant at approximately two months of age, as growing in a nursery pot.
Figure 2:
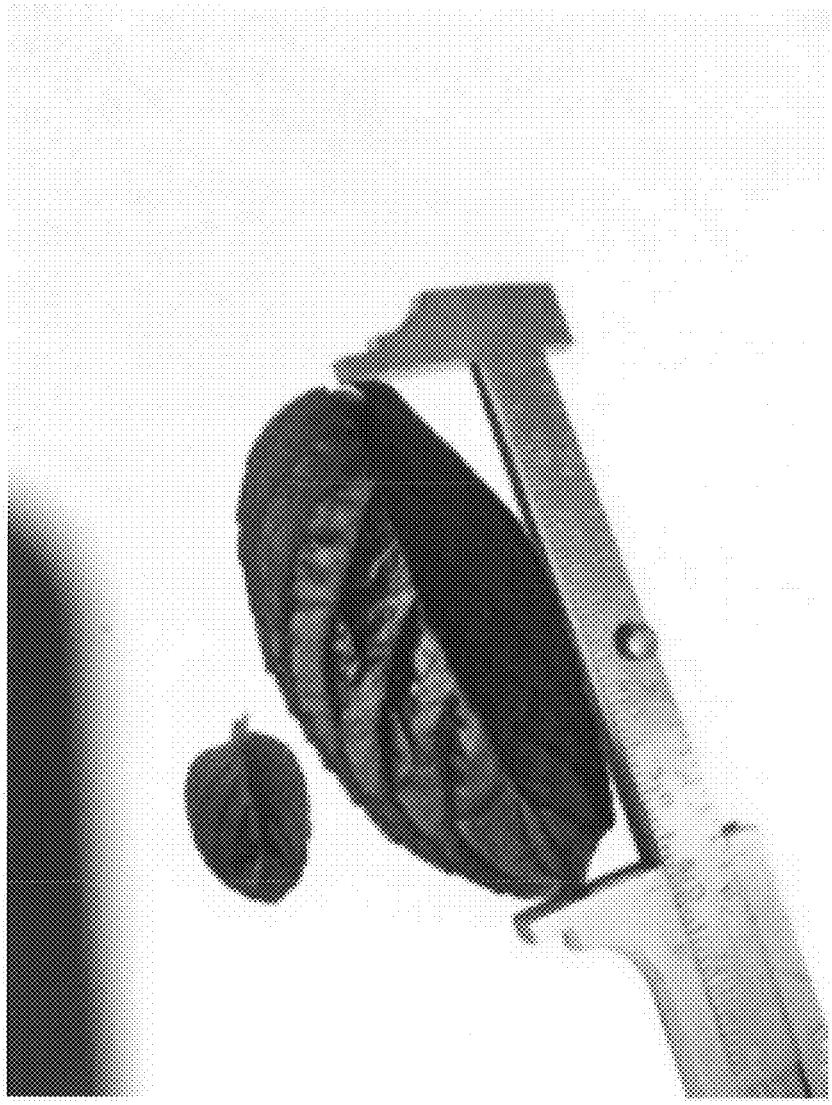
FIG. 2 illustrates an immature next to a mature leaf of a 'MP18' mint plant at approximately two months of age.
Figure 3:
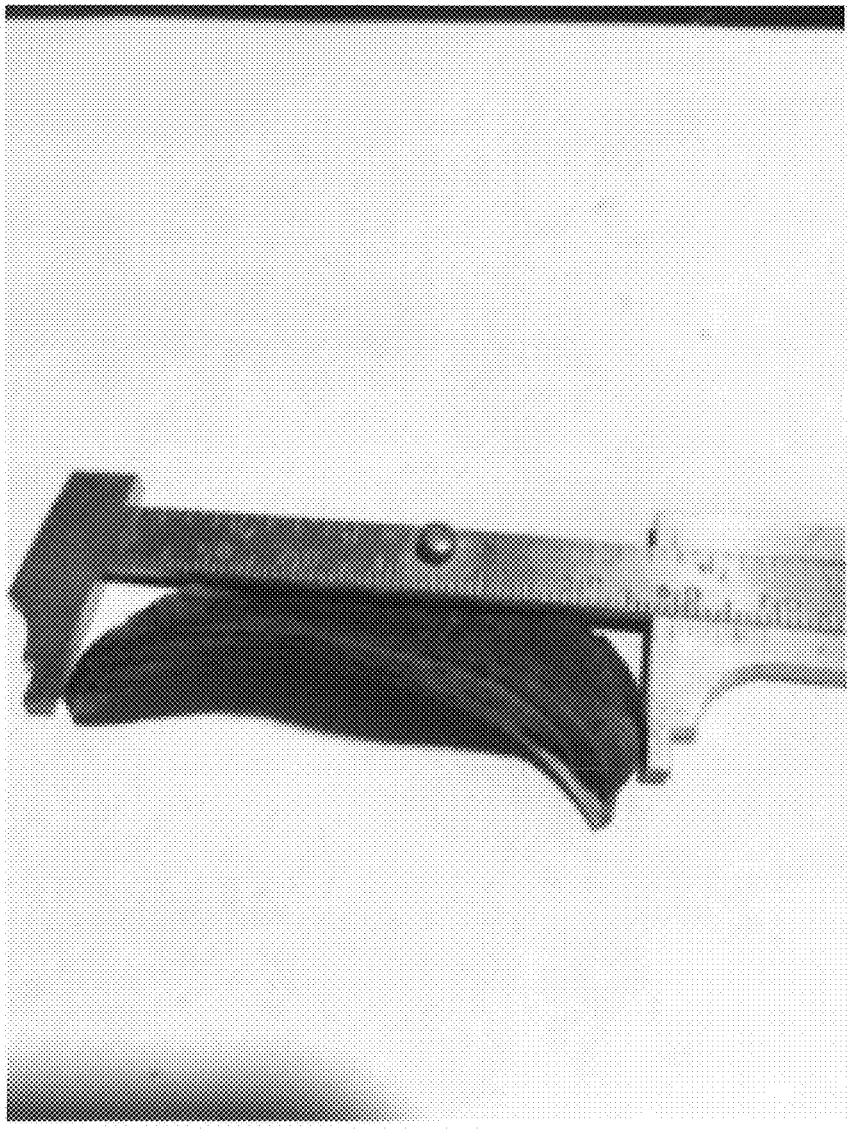
FIG. 3 illustrates a mature leaf of a 'MP18' mint plant at approximately two months of age.
Figure 4:
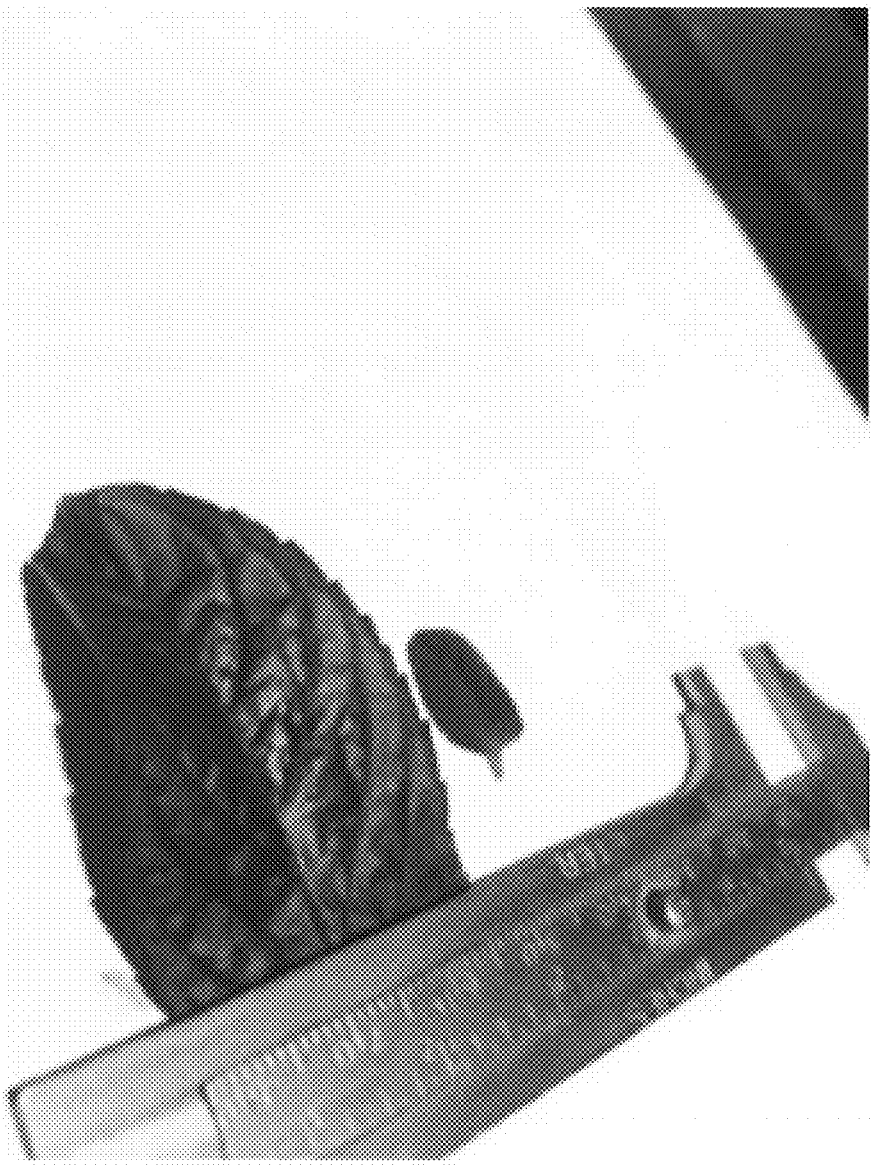
FIG. 4 illustrates an immature next to a mature leaf of a 'MP18' mint plant at approximately two months of age.
Figure 5:
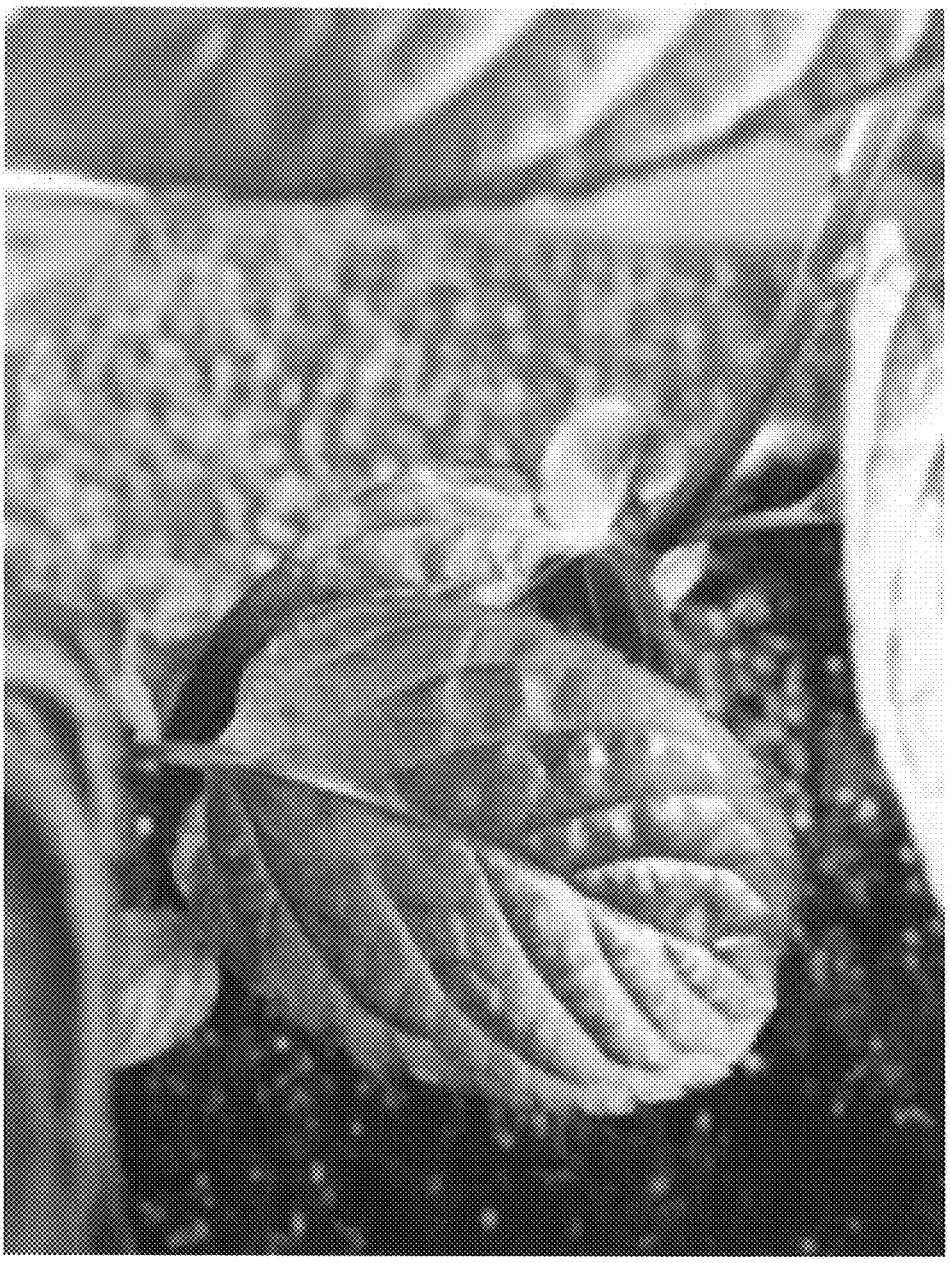
FIG. 5 illustrates the leaves of a maturing 'MP18' mint plant as growing in a nursery pot at approximately two months of age.
Figure 6:
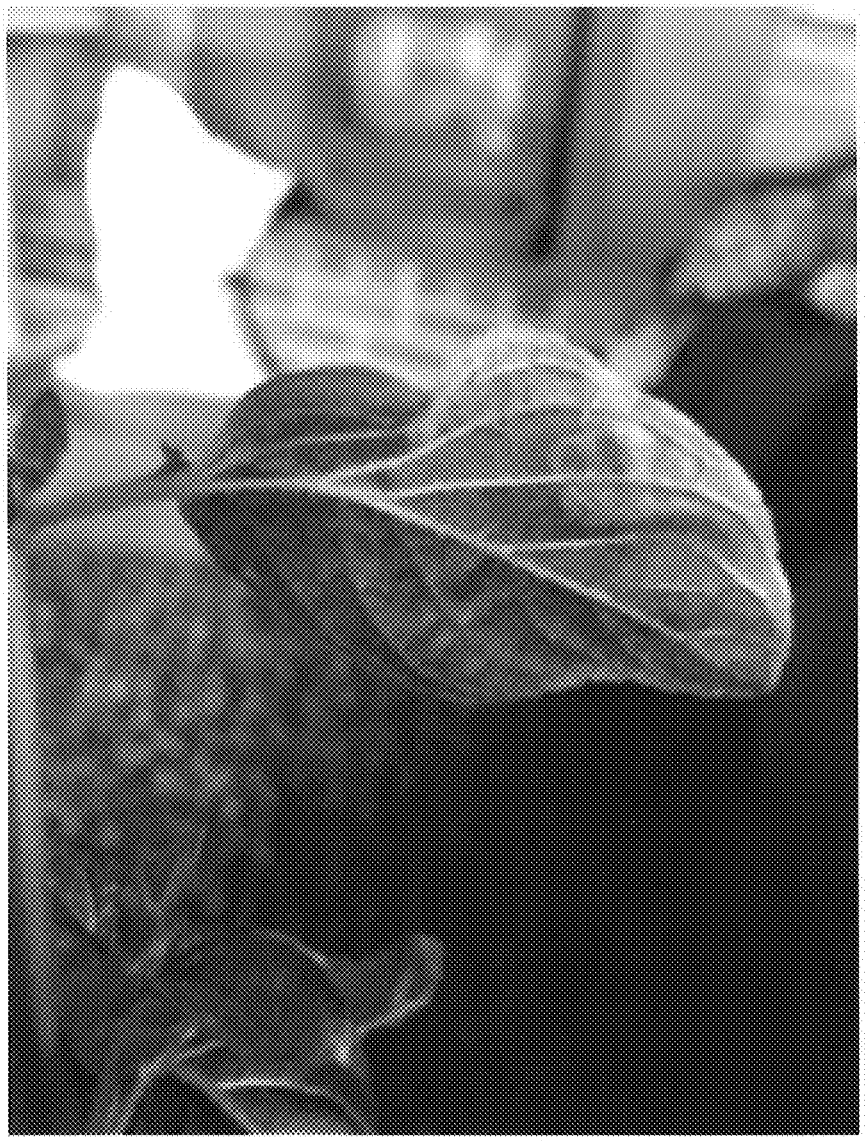
FIG. 6 illustrates a maturing 'MP18' mint plant as growing in a nursery pot at approximately two months of age.
Figure 7:
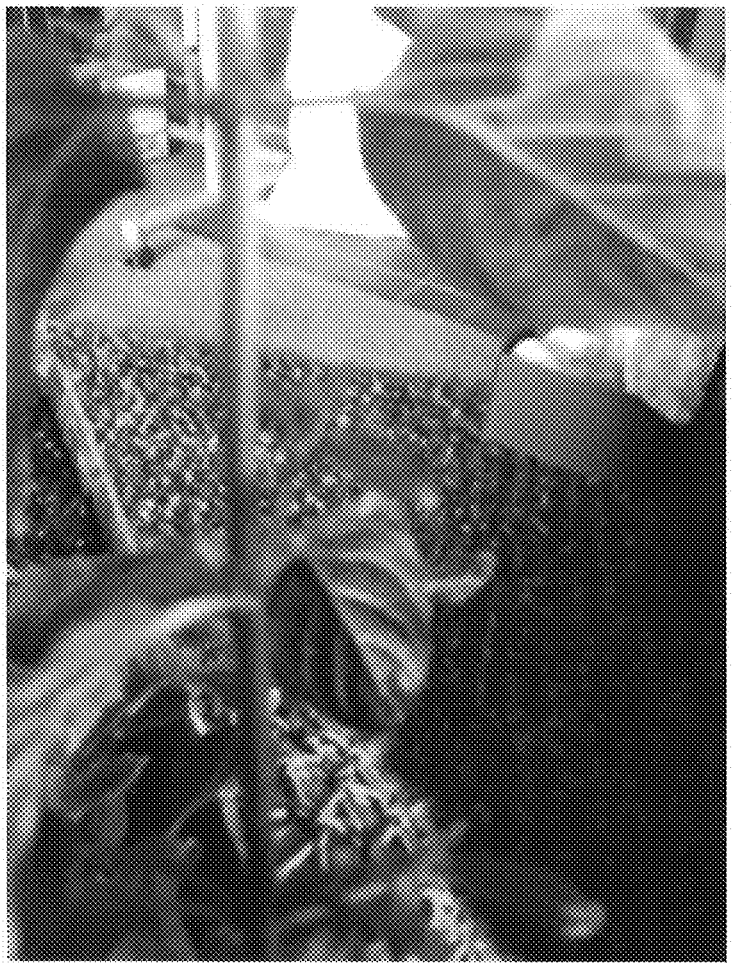
FIG. 7 illustrates a maturing 'MP18' mint plant as growing in a nursery pot at approximately two months of age.
Figure 8:
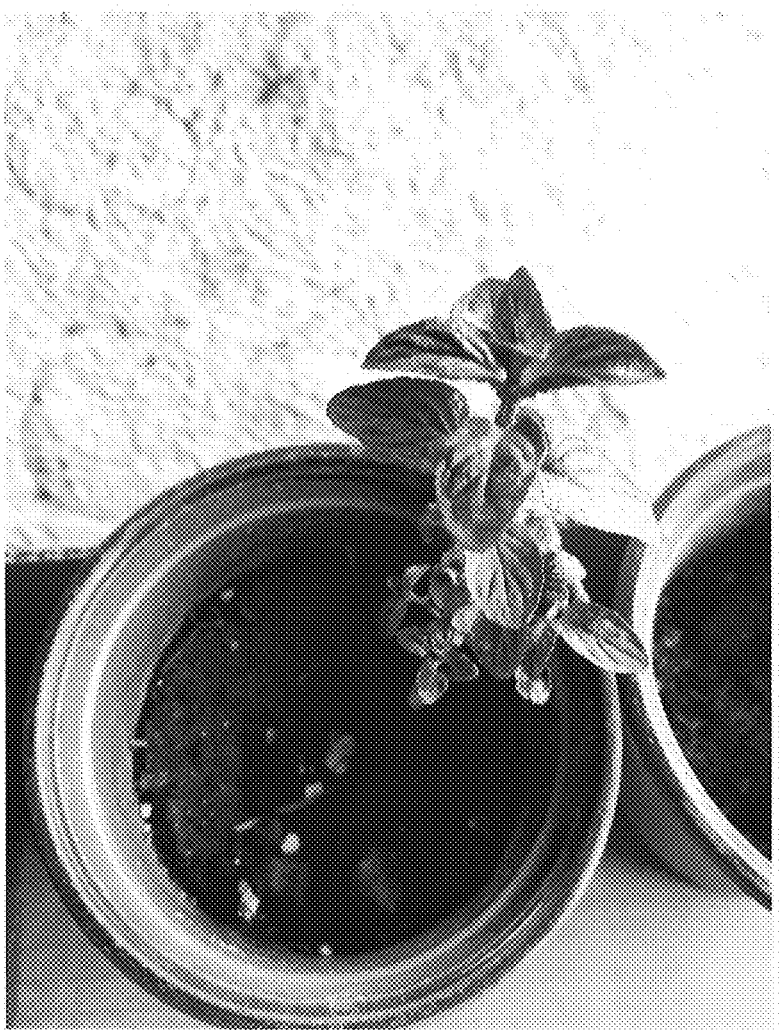
FIG. 8 illustrates a maturing 'MP18' mint plant as growing in a nursery pot at approximately two years of age.
Figure 9:
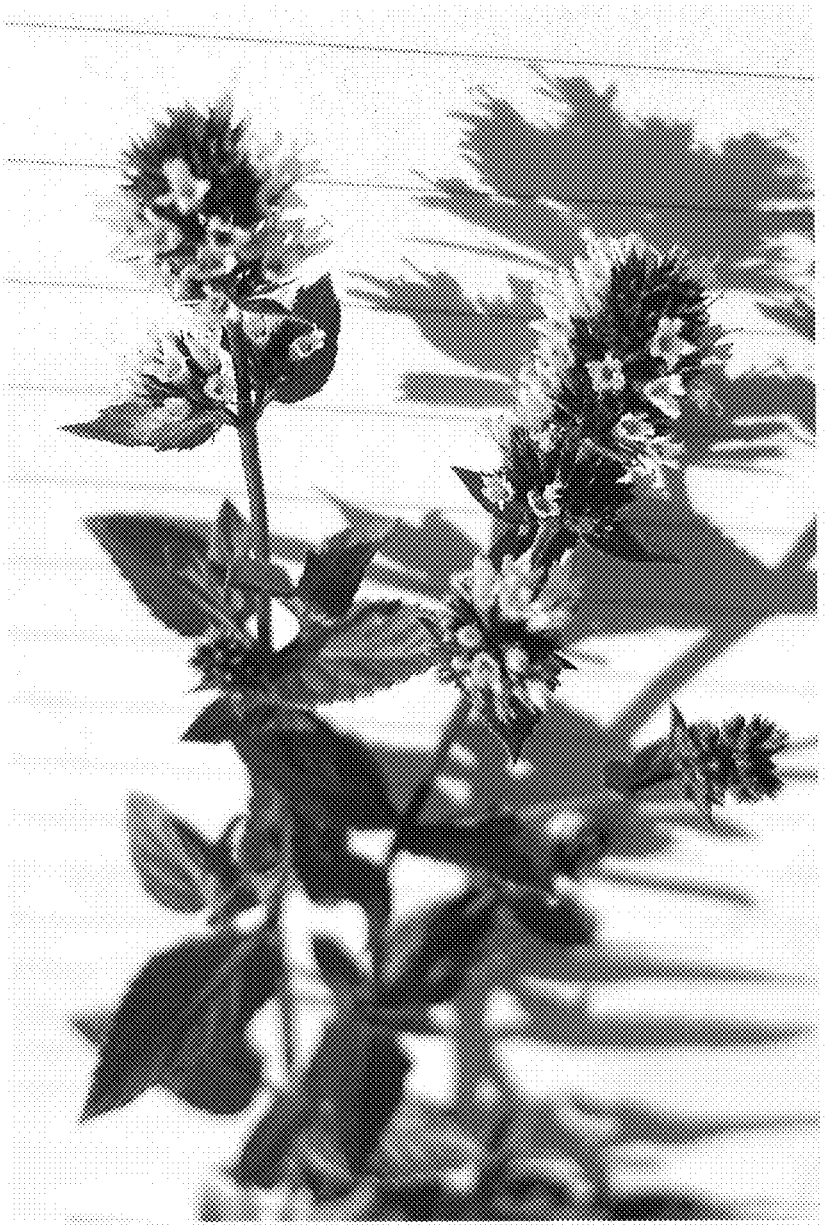
FIG. 9 illustrates a mature flowering 'MP18' mint plant pot at approximately two years of age.
Figure 10:
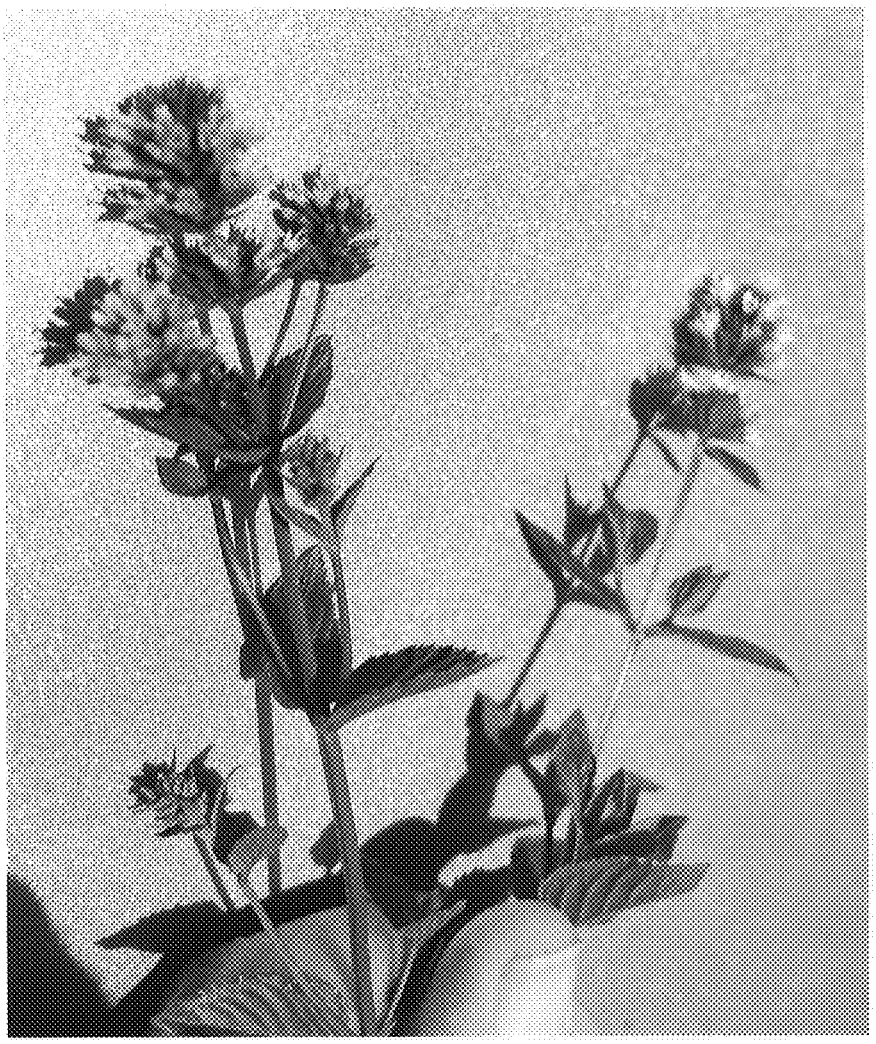
FIG. 10 illustrates a mature flowering 'MP18' mint plant pot at approximately two years of age.

The colors of these illustrations may vary with lighting conditions and, therefore, color characteristics of this new variety should be determined with reference to the observations described herein, rather than from these illustrations alone.

DETAILED BOTANICAL DESCRIPTION

The following description is based on observations of the new 'MP18' mint plant made in 2021 near Yakima, Wash. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant or any group of plants, of the new variety may vary from the stated average.

The leaves of the 'MP18' mint plant have the rough edges of *Mentha spicata* (common name, spearmint), with a general shape and texture more similar to *Mentha* x *piperita f. citrata*, (common name, chocolate mint). The 'MP18' has a *Mentha suaveolens* 'Variegata' (common name, pineapple mint), flavor in steeped reduction, and a burgundy or "anthocyanin" edge color, to make the 'MP18' leaf distinguishable from the parent, chocolate mint, which may only exhibit the burgundy colorations at its leaf margins and on its stems. The *Mentha suaveolens* (common name apple mint), introduced a diffuse texture to the leaves and a menthol flavoring. The chocolate mint female parent contributes the most repetition in flavor profiling in 'MP18', comparable to related spearmint plants in *Mentha suaveolens* hybrid modification series, which imparts a sweeter taste to the flavor profile but with dry leaf products than the parent plants.

In comparison to 'MP18', *Mentha suaveolens* (common name, apple mint), exhibits opposite, wrinkled, sessile leaves, typically between 3 cm to 5 cm long and 2 cm to 4 cm wide, and being somewhat hairy on top and downey underneath with finely serrated edges. In contrast, the 'MP18' leaf blades are more pronouncedly serrated; and conduplicate toward base and slightly flattening distally, with coarse undulation about 10 mm deep with arcuate venation, while being glabrous abaxial, slightly glaucous and canescent adaxial, and additionally with dark burgundy margins, typically developing toward apex on some leaves.

Also, in comparison to 'MP18', *Mentha* x *piperita f. citrata* (common name, chocolate mint) exhibits smooth, dark green leaves, with purplish to brownish tints, and are typically lance-shaped with a toothed leaf margin, and being somewhat hairy on top and downey underneath with finely serrated edges, and slightly chordate at the base. In contrast, the 'MP18' leaf blades are more pronouncedly ovate in form; and conduplicate toward base and slightly flattening distally, while being glabrous abaxial, slightly glaucous and canescent adaxial, and additionally with dark burgundy margins, typically developing toward apex on some leaves.

Preferably, the leaves of the 'MP18' mint plant are used in botanical beverages, with a diminished intensity of menthol compared to the parent 'chocolate mint', as achieved through the inventor's selective plant pollination process.

The refined 'MP18' mint plant exhibits burgundy, anthocyanin coloration bordering the leaves and petioles of plant, with some similarity to the leaf profile patterns and colors of *Mentha spicata* (common name, spearmint). The burgundy of the *Mentha* x *piperita* (common name, peppermint) plant replaces the lighter green colorations of the chocolate mint, as employed to augment the hybrid 'MP18' mint plant.

The following descriptions and color references are based on the 2019 reprint of the 2015 edition of The Royal Horticultural Society Colour Chart (R.H.S.), except where common dictionary terms are used.

The new mint plant, 'MP18', has not been observed under all possible environments. The phenotype may vary slightly with different environmental conditions, such as temperature, light, fertility, moisture and maturity levels, but without any change in the genotype.

The following observations and size descriptions are of a two-year old plant in a commercial wholesale greenhouse located in East Selah, near Yakima, Wash., with supplemental water and fertilizer, as needed.

Botanical classification: *Mentha suaveolens* x *piperita.*

Variety denomination: 'MP18'.

Parentage: 'MP17' as female (seed) parent, and *Mentha* x *piperita f. citrata*, (common name, chocolate mint) as male (pollen) parent, with 'MP17' a result of a cross between *Mentha suaveolens* (common name apple mint) and *Mentha suaveolens* 'Variegata' (common name, pineapple mint), and male parent *Mentha* x *piperita f. citrata*, (common name, chocolate mint).

Propagation: Controlled pollination cross, followed by plant division with herbaceous cuttings.

Growth rate: Moderate to rapid.

Crop time: About 10 to 14 weeks to finish during lengthening spring days from an established rhizome tissue plug to a 65 mm diameter container.

Rooting habit: Fleshy, lightly branching, with roots up to 15 cm long.

Root color: RHS Pale Yellow 158B.

Plant shape and habit: Branches in compact secondary and tertiary pattern to form a compact growth habit. The main stem typically at mid-plant in a mature plant is approximately 5 mm in width and the secondary branch stems are approximately 1.5 mm in width. The average overall plant width is approximately 30 cm and the average length of the main stem is approximately 150 cm in length.

Plant size: Foliage height about 25 cm tall from soil line to the top of the leaves and about 10 cm wide at the widest point at the lower portion of the plant.

Foliage description: Ovate; simple; opposite and decussate; serrulate margins with flexible teeth, teeth about 0.5 mm long and spaced about 2.0 mm apart; acute apex; base slightly truncate, petiolate.

Number of leaves: About 40 per plant.

Leaf blades: Serrate; to about 30 mm long, about 20 mm wide at base and 1.0 mm thick, average about 28.0 mm long, 15 mm wide and 0.9 mm thick; typically conduplicate toward base slightly flattening distally, with coarse undulation about 10 mm deep and bi-laterally symmetrical; arcuate venation; glabrous abaxial and slightly glaucous and canescent adaxial; with dark burgundy margins typically developing toward apex on some leaves.

Leaf blade color:

*Adaxial.*—Upper surface (young): Nearest RHS 138A.

*Abaxial.*—Lower surface (young): RHS 138B.

*Adaxial* (*mature*).—RHS 137B; with anthocyanin coloration intensifying with ultraviolet light exposure to RHS N79A.

*Abaxial* (*mature*).—RHS 138A; with anthocyanin coloration intensifying with ultraviolet light exposure to RHS N79A.

*Teeth.*—RHS 138A; with anthocyanin coloration intensifying with ultraviolet light exposure to RHS N79A.

Petiole: Stipulate, RHS 147C; glabrous with anthocyanin coloration increasing upon ultraviolet light exposure to RHS N79A.

Veins: Arcuate on approach to leaf margin.

Flowers: The inflorescences of 'MP18' are compound dichasium in form with rounded thyrsoid clusters of lobed tube flowers developing at the nodes of the peduncle.

*Distance between peduncle nodes.*—1 cm to 4 cm.

*Average number of flowers per inflorescence.*—Varies greatly, typically with 20 to 80 flowers per inflorescence. Average length of the pedicel ranges from sessile for immature blooms to 30 mm in length for mature blooms.

*Peduncle color*.—RHS 147C; glabrous with anthocyanin coloration increasing upon ultraviolet light exposure to RHS N79A.

*Flowers*.—Tubular capitates, each 1.5 mm to 2.0 mm in length, and 0.8 mm to 1.2 mm in width.

*Inflorescence petals*.—A four lobed tubular corolla.

*Androecium*.—Two filantherous stamens per flower (diandrous), each with a distinct filament and anther of less than 1 mm in length.

*Corolla color*.—Adaxial and abaxial surfaces of the corolla are initially light violet RHS N88D, and fade to very pale purple RHS 91C and then to white in the mature flower.

*Calyx color*.—Strong yellowish-green RHS 135C.

*Gynoecium*.—A single pistil with two lobed, exserted stigma.

*Styles*.—Macrostylous with lengths in mature flower of approximately 20 mm.

*Anthers*.—Less than 1 mm in length.

*Filaments*.—Range from 0.5 mm to 4.0 mm in length.

*Ovaries*.—Approximately 0.5 mm in width.

*Pollen*.—Little produced.

*Flower fragrance*.—None observed.

The flavor profile of a beverage brewed with the 'MP18' mint plant has light menthol taste, without losing the flavor qualities of peppermint or of chocolate mint. Sequencing pineapple mint into the peppermint flavoring of chocolate mint through selective isolated pollination, served to diminish the menthol essential oil's power in the 'MP18' leaf products, as used in a dry leaf product used for beverages, culinary and non-tobacco products. Leaves of the 'MP18' mint plant store oil that is released in both hot water and cold water. The flavor profile of the 'MP18' mint plant complements other flavors that would not taste appealing and contrast with the strong menthol characteristics of leaves of the peppermint or the chocolate mint plants. Again, by the reduction of menthol as compared to other mint plants, the flavor profile of the 'MP18' mint plant is somewhat neutralized but kept the spearmint flavor profile from the peppermint plant, quickening the bio-availability of the 'MP18' mint plant as compared with other mint family herbs in tandem species through the combination, mixing, and unique formulation realized in the inventor's hybridization.

The invention claimed is:

1. A new and distinct variety of Mint plant named 'MP18', substantially as illustrated and described herein.

* * * * *